(12) United States Patent
Miller et al.

(10) Patent No.: US 8,178,519 B2
(45) Date of Patent: *May 15, 2012

(54) PHARMACEUTICAL MANUFACTURING PROCESS FOR HEAT STERILIZED GLUCOCORTICOID SUSPENSIONS

(75) Inventors: John Miller, Cheshire (GB); Paul Ronald, Cheshire (GB); Adrian Ashley, Cheshire (GB); Paul Lamb, Cheshire (GB); Donald MacDonald, Cheshire (GB); Martin Oliver, Cheshire (GB); Matthew Pollard, Cheshire (GB)

(73) Assignee: Norton Healthcare Limited, London (GB)

(*) Notice: Subject to any disclaimer, the term of this patent is extended or adjusted under 35 U.S.C. 154(b) by 1068 days.

This patent is subject to a terminal disclaimer.

(21) Appl. No.: 11/667,872

(22) PCT Filed: Nov. 16, 2005

(86) PCT No.: PCT/US2005/041524
§ 371 (c)(1),
(2), (4) Date: Jan. 14, 2008

(87) PCT Pub. No.: WO2006/055632
PCT Pub. Date: May 26, 2006

(65) Prior Publication Data
US 2008/0269178 A1    Oct. 30, 2008

(30) Foreign Application Priority Data
Nov. 16, 2004    (GB) .................................. 0425266.4

(51) Int. Cl.
*A61K 31/58* (2006.01)
*A61K 31/56* (2006.01)
(52) U.S. Cl. ......... 514/174; 514/176; 514/178; 514/180
(58) Field of Classification Search ................... 514/174, 514/176, 178, 180
See application file for complete search history.

(56) References Cited

U.S. PATENT DOCUMENTS

| | | | |
|---|---|---|---|
| 3,962,430 A | 6/1976 | O'Neill | |
| 5,993,781 A | 11/1999 | Snell et al. | |
| 6,066,292 A | 5/2000 | Purwar | |
| 6,392,036 B1 | 5/2002 | Karlsson et al. | |
| 6,464,958 B1 | 10/2002 | Bernini et al. | |
| 2002/0065256 A1 | 5/2002 | Karlsson et al. | |
| 2003/0103864 A1* | 6/2003 | McAffer et al. | 422/1 |
| 2006/0140816 A1 | 6/2006 | Gentile et al. | |
| 2008/0139519 A1 | 6/2008 | Ashley et al. | |

FOREIGN PATENT DOCUMENTS

| | | |
|---|---|---|
| DE | 10145361 A1 | 3/2003 |
| DE | 101 45 361 A1 | 4/2003 |
| EP | 1 454 636 A1 | 9/2004 |
| WO | WO-9531964 | 11/1995 |
| WO | WO-99/32156 A2 | 7/1999 |
| WO | WO-99/36055 A1 | 7/1999 |
| WO | WO-00/25746 A2 | 5/2000 |
| WO | WO-0025746 A2 | 5/2000 |
| WO | WO-02/41925 A1 | 5/2002 |
| WO | WO-03/086347 A1 | 10/2003 |
| WO | WO-2004/078102 A2 | 9/2004 |
| WO | WO-2004/082659 A1 | 9/2004 |
| WO | WO-2005/115332 A2 | 12/2005 |

OTHER PUBLICATIONS

Illum et al., "Surface area stability of micronized steroids sterilized by irradiation," *Arch. Pharm. Chemi. Sci.*, Ed. 2, 1974, pp. 167-174.
Office Action dated Mar. 11, 2010 for U.S. Appl. No. 10/594,861.
Office Action dated Aug. 3, 2009, U.S. Appl. No. 10/594,861.

* cited by examiner

*Primary Examiner* — Barbara P Badio
(74) *Attorney, Agent, or Firm* — RatnerPrestia (57) ABSTRACT

The present invention provides a method for preparing a sterile suspension of a glucocorticosteroid. The glucocorticosteroids used in the invention are preferably antiinflammatory glucocorticosteroids. By making the last stage of product preparation be the sterilization process, the potential for contamination during manufacture and heat degradation of products is greatly reduced.

19 Claims, 3 Drawing Sheets

Fig. 5

PHARMACEUTICAL MANUFACTURING PROCESS FOR HEAT STERILIZED GLUCOCORTICOID SUSPENSIONS

This application is the U.S. National Phase application of PCT International Application No. PCT/US2005/041524, filed Nov. 16, 2005, and claims priority of British Patent Application No. 0425266.4, filed Nov. 16, 2004.

TECHNICAL FIELD OF THE INVENTION

The present invention relates to a pharmaceutical manufacturing process and particularly to a process for sterilizing glucocorticosteroids.

BACKGROUND OF THE INVENTION

Sterile drug products provide a number of benefits, both medically and economically. The medical ramifications requiring sterile drug preparations are clear in that the use of non-sterile preparations may subject the patient to an unnecessary risk of secondary infection from the contaminating microbe, a microbe that is at least resistant to the drugs of the preparation. Furthermore, even if the contaminant is innocuous, the growth can result in loss of active drug products per se with possible concomitant generation of toxic by-products. Economically, contaminated drug products have a shortened shelf life, which requires increased production expenses to replace product on a more frequent basis.

Methods are needed for the preparation of sterile products for patient use. However, the problem associated with many sterilization procedures is that the process often results in unfavorable changes in the drug profile. These changes in the drug profile can range from loss of activity, to increased degradation products being created, or possible alteration of the chemical or physical characteristics of the compound sterilized. These problems are especially pronounced when glucocorticosteroids are sterilized.

Sterilization of materials relies on the input of sufficient energy to be lethal to any potential microbial contamination. Numerous methods including heat, radiation, and chemicals have been proposed for the sterilization of glucocorticosteroids. However, to date these methods often result in the excess production of degradants or a loss of activity for the glucocorticosteroid being sterilized. Additionally, as in the case of glucocorticosteroid suspension formulations for metered dose inhalation, the commonly used sterilization procedures often results in unacceptable changes to drug particle size.

Chemical sterilization, for the most part, has been based on exposure to toxic compounds, for example, ethylene oxide. However, when used to sterilize glucocorticosteroids, ethylene oxide has been found to leave residual amounts of ethylene oxide in the drug preparation. Ethylene oxide is toxic and the residual levels are often above the pharmaceutically acceptable limits as set by most regulatory agencies.

Irradiation based sterilization is known and has been recommended for glucocorticosteroids (see Illum and Moeller in *Arch. Pharm. Chemi. Sci.*, Ed. 2, 1974, pp. 167-174). However, significant degradation has been reported when irradiation has been used to sterilize micronized glucocorticosteroids.

WO 00/25746 (Chiesi) discloses a process for preparing a suspension of a glucocorticosteroid. In a first step an aqueous carrier is mixed in a turboemulsifier and sterilized by heat treatment or filtration. In a second step a micronized active ingredient (e.g. a glucocorticosteroid), pre-sterilized by gamma irradiation, is added to the aqueous carrier.

WO 03/086347 (Chiesi) describes some of the disadvantages of WO 00/25746 and discloses an improvement in the process whereby the active ingredient is introduced into a turboemulsifier as a powder by exploiting the vacuum in the turboemulsifier. Again the active ingredient is sterilized prior to dispersion in the aqueous carrier.

Neither of these documents disclose the sterilisation by heating of an aqueous suspension of a glucocorticosteroid and hence the problem of particle size growth during the heating and subsequent cooling steps is not addressed.

U.S. Pat. No. 3,962,430 (O'Neill) discloses a method for the production of sterile isotonic solutions of medicinal agents. The method comprises adding the medicinal agent to a saturated solution of sodium chloride in water at 100° C. The drug/saturated sodium chloride solution is then heated to 100-130° C. This method, which purportedly is based on the theory that the sodium chloride ions tie up free water thereby preventing hydrolytic degradation, is not suitable for suspensions of fine particles of glucocorticosteroids intended for inhalation, as the procedure produces unfavorable changes in the size of the particles. Additionally, the procedure can result in bridge formation between drug particles producing large aggregates, which do not break up on administration.

In order to address the problem of particle growth, U.S. Pat. No. 6,392,036 (Karlsson) discloses a method for the dry heat sterilization of powdered glucocorticosteroids that can then be used for drug formulations. However, this method results in unacceptable levels of heat-degradation products.

WO 2004/078102 (Dompe) discloses a method for sterilizing an aqueous suspension of a glucocorticosteroid consisting of the glucocorticosteroid and water only. Minimal detail is provided of the sterilisation apparatus.

SUMMARY OF THE INVENTION

The present invention provides a method for preparing a sterile suspension of a glucocorticosteroid comprising the following steps: (i) heating a glucocorticosteroid suspension comprising a glucocorticosteroid, water and a surfactant in a mixing vessel to sterilize the glucocorticosteroid suspension, (ii) re-circulating the glucocorticosteroid suspension via a homogenizer before, during and/or after step (i), and subsequently, (iii) mixing the glucocorticosteroid suspension with sterile water or a sterile excipient liquid comprising water and one or more pharmaceutically acceptable excipients.

DETAILED DESCRIPTION OF THE INVENTION

As used herein, "glucocorticosteroid" refers to any of a group of steroid hormones (including derivatives, synthetic analogs, and pro-drugs), such as cortisone, which are produced by the adrenal cortex. These compounds are involved in carbohydrate, protein, and fat metabolism. Additionally, the glucocorticosteroids may have anti-inflammatory properties.

Non-limiting examples of glucocorticosteroids, which may be used in the present invention, include beclomethasone, budesonide, ciclesonide, cortivazol, deflazacort, flumethasone, flunisolide, fluocinolone, fluticasone, mometasone, rofleponide, tipredane and triamcinolone. Preferably, use is made of budesonide, beclomethasone (e.g. the dipropionate), ciclesonide, fluticasone, mometasone and triamcinolone. Most preferably, use is made of budesonide and beclomethasone (e.g. the dipropionate).

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention.

The patent and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

In the specification and the appended claims, singular forms, including the singular forms "a," "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or."

As used in this specification, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Figure 1:
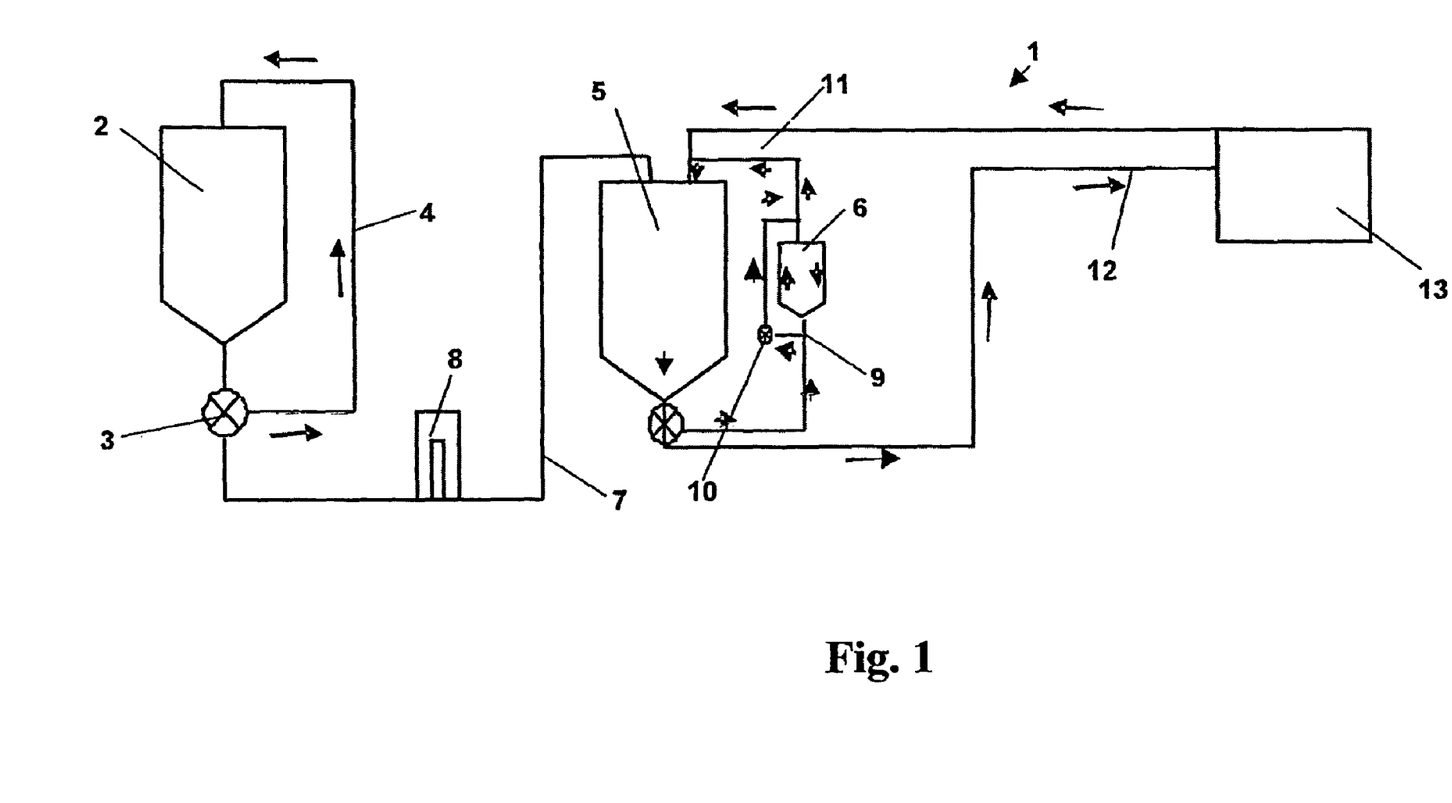
FIG. 1: Representation of the apparatus used for the sterilization of a suspension of a glucocorticosteroid in accordance with the present invention.
Figure 2:
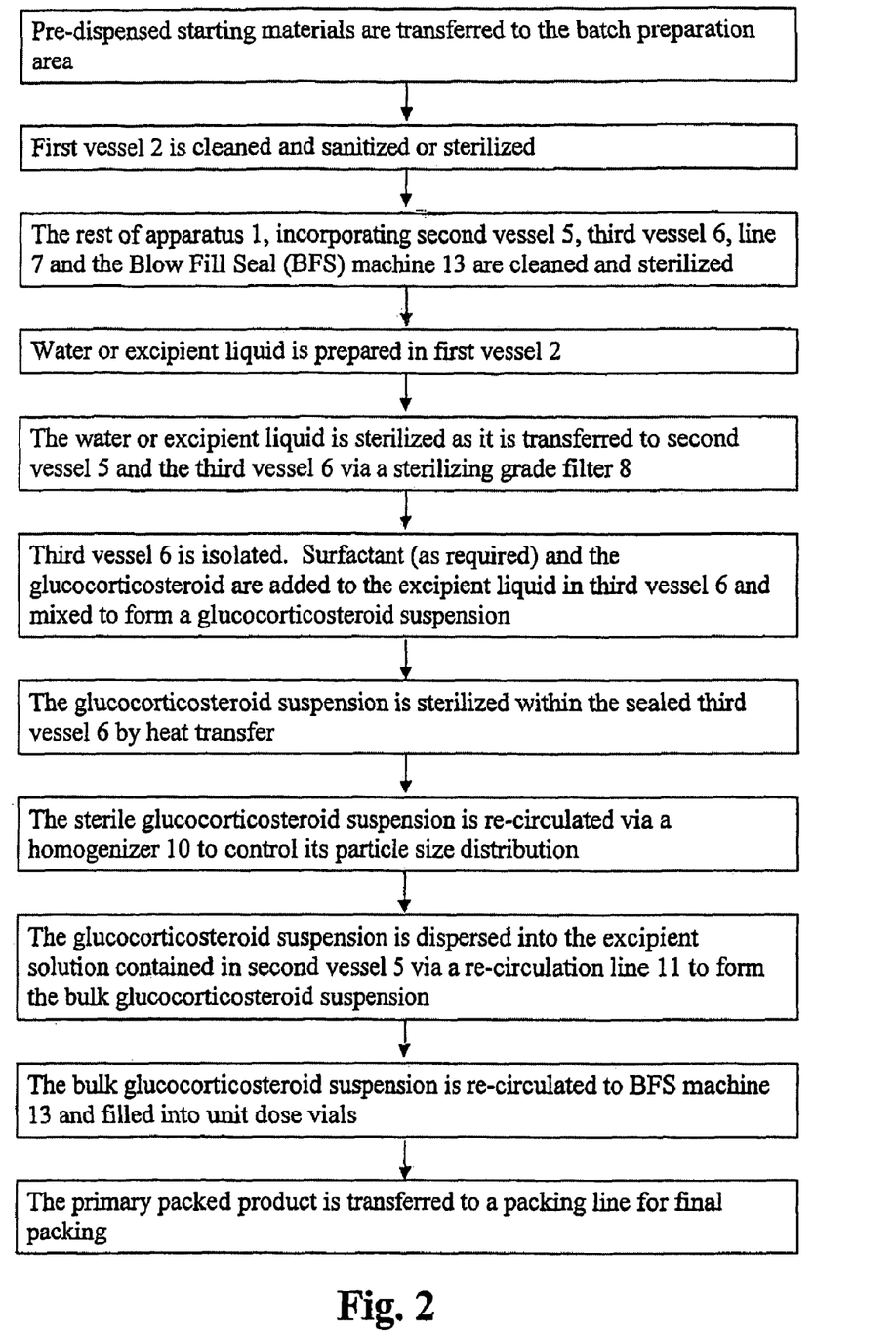
FIG. 2: Flow chart showing the methodology for the sterilization of the suspension of the glucocorticosteroid using the apparatus represented in FIG. 1.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the inventor as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention FIG. 1 shows a schematic representation of the apparatus 1 used to manufacture and fill batches of a sterile glucocorticosteroid suspension. An excipient liquid, preferably an excipient solution, is prepared in a first vessel 2. Alternatively, the first vessel 2 is simply charged with water. The first vessel 2 is provided with a mixer 3 and a re-circulation line 4. A concentrated glucocorticosteroid suspension is then manufactured and sterilized before being diluted with the sterile water or sterile excipient liquid. Accordingly, the apparatus 1 is provided with second and third vessels 5 and 6. The second and third vessels 5 and 6 are connected to the first vessel 2 by line 7 having a sterilizing-grade filter 8. Before, during and/or after the sterilization of the concentrated glucocorticosteroid suspension, the suspension is re-circulated via re-circulation line 9 and homogenizer 10. After sterilization the sterilized concentrated glucocorticosteroid suspension is passed via re-circulation line 11 for dilution with the sterile water or excipient liquid in the second vessel 5. The suspension is then passed via line 12 for packaging into suitable containers at blow-fill-seal (BFS) machine 13. These process steps are summarized in FIG. 2.

Each step will now be described in more detail.

The excipient liquid is prepared in a first vessel 2. Prior to mixing, the first vessel 2 is cleaned and either sanitized or sterilized in place, for example using hot water for injections (WFI) followed by steam sanitization using steam at temperatures of not less than 100° C. for not less than 15 mins. After sanitization or sterilization the water is introduced or the excipient liquid is prepared as required. The excipient liquid comprises water and a pharmaceutically acceptable excipient, such as a surfactant and preferably further comprises other pharmaceutically acceptable excipients, diluents, etc., such as at least one buffer, at least one salt, and at least one wetting agent, stabilizing agent and/or isotonic agent. Pharmaceutically acceptable surfactants are well known in the art and are exemplified by Polysorbates, e.g. Polysorbate 80. The components may be added in any order although preferably the required quantity of water, e.g. WFI, is charged into the mixing vessel followed by the other components which are added to the circulating water via an additions hopper (not shown).

Preferably at least about 50%, more preferably about 70-90% of the total quantity of surfactant required in the sterile glucocorticosteroid suspension is added at this stage. Following this addition, the additions hopper is rinsed with the circulating solution and the solution is mixed, e.g. for 10 mins, to ensure complete dissolution using a mixer 3 and re-circulation line 4 to form the excipient liquid which is preferably a homogenous excipient solution.

A concentrated suspension of a glucocorticosteroid is prepared and sterilized in the third vessel 6 (also termed the "concentrate vessel"). The third vessel 6 has a re-circulation line 9 incorporating a homogenizer 10. However, prior to sterilisation of the glucocorticosteroid suspension, the remainder of the apparatus 1 including the second vessel 5, the third vessel 6 and the filtration line 7 as well as any additional components, may be cleaned and sterilized in place, for example using hot WFI followed by steam at temperatures of about 122° C. to about 138° C. for not less than 30 mins. Following sterilization, second vessel 5 and any other cleaned and sterilized components of apparatus 1 are continuously held under positive pressure to maintain the sterility of the system and contents during subsequent batch manufacture and filling. The positive pressure may be maintained using sterile compressed air.

The water or excipient liquid is sterilized and the second vessel 5 and the third vessel 6 are charged with the water or excipient liquid. Sterilization of the water or excipient liquid is completed by filtration via a sterilizing grade filter 8 during transfer of the water or excipient solution from first vessel 2 to both the second vessel 5 and the third vessel 6. However, alternative methods of sterilization could be employed, such as heat-treating the excipient liquid.

The third vessel 6 is isolated from second vessel 5 and the third vessel 6 is opened. At this stage surfactant is added to the water or additional surfactant may be added to the excipient liquid in the third vessel 6 in order to facilitate formation of a stable suspension. Preferably the concentration of the surfactant in the concentrated glucocorticosteroid suspension is from about 0.2 to about 300, more preferably from about 0.2 to about 60 mg/ml. The glucocorticosteroid is then added to the third vessel 6. The glucocorticosteroid does not need to have been sterilized at this stage. An overage of the glucocorticosteroid may be added if there are any process losses of the glucocorticosteroid during bulk product suspension manufacture and filling.

The concentration of the glucocorticosteroid in this "concentrated" glucocorticosteroid suspension is preferably from about 15 to about 300, more preferably about 15 to about 150 mg/ml. In addition, it is preferred that at least 50% of the glucocorticosteroid in the glucocorticosteroid suspension is in the form of a suspension during heating, the remainder being held in solution. More preferably, at least 60% is in the form of a suspension.

The third vessel 6 is then sealed. The contents of the third vessel 6 are preferably re-circulated, e.g. for at least about 1 min, preferably for at least about 10 mins forming a homogenous suspension of glucocorticosteroid.

The third vessel 6 has at least two openings served by a re-circulation line 9. The re-circulation line 9 allows the content of the third vessel 6 to be removed from the third vessel 6 at a first opening and re-charged into the third vessel 6 at a second opening. It is preferred that the first opening is at the bottom of the third vessel 6 and that the second opening is at the top. The force required to re-circulate the content is provided by the homogenizer 10. The content of the third vessel 6 is also caused to pass through the homogenizer 10 as it is re-circulated. Since homogenisation of the content, i.e. the glucocorticosteroid suspension, occurs as it passes through the re-circulation line 9, the third vessel 6 does not require any internal mechanism for agitation of the content. Indeed, in a preferred embodiment, the third vessel 6 is free of any agitation mechanism and most preferably the third vessel 6 consists essentially of a metallic (e.g. stainless steel) casing having a plurality of openings for charging and evacuating the vessel. Whilst the shape of the third vessel 6 is not critical, in order to avoid any dead space where the content may become trapped and unable to be evacuated, the third vessel is preferably cylindrical and more preferably has a conical bottom tapering towards the first opening. The simplicity of the third vessel 6 is particularly advantageous since it reduces the number of working parts and the overall surface area onto which the glucocorticosteroid suspension comes in contact, thereby reducing any loss of drug by adhesion to the surfaces, reducing the possible sources of contamination and reducing the time required for cleaning the apparatus.

Heat is applied to the sealed third vessel 6 using a heater 14, such as a steam jacket. The glucocorticosteroid suspension, third vessel 6, re-circulation line 9 and homogenizer 10 are sterilized in situ via heat transfer from the heater. Heating is carried out at a sterilizingly effective temperature for a sterilizingly effective time, preferably at a temperature of from about 101 to about 145° C., more preferably from about 122° C. to about 138° C., for about 2 to about 180 mins, more preferably for at least about 30 mins.

Figure 3:
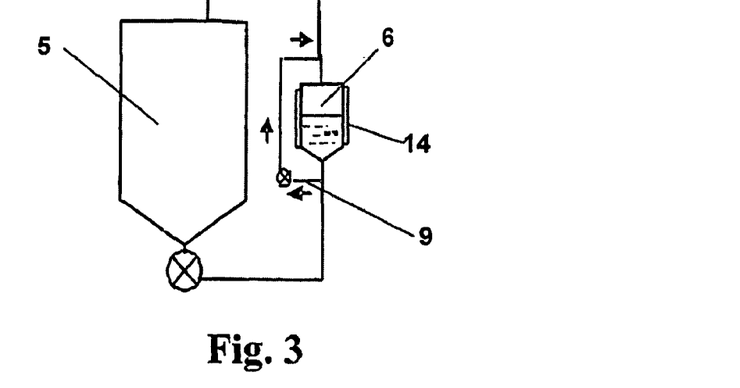
FIGS. 3-5: Representation of specific parts of the apparatus represented in FIG. 1.

At this stage, the glucocorticosteroid suspension is circulated around the third vessel 6, re-circulation line 9 and homogenizer 10 to ensure effective sterilization of the system and glucocorticosteroid suspension. FIG. 3 shows the re-circulation of the glucocorticosteroid suspension during heat sterilization detailing the re-circulation line 9. Optionally, the concentrate may be pre-treated to reduce the particle size distribution of the glucocorticosteroid to a pre-specified value, including by circulation through the homogenizer. The glucocorticosteroid suspension is preferably circulated during the heating step although it may alternatively, or in addition, be circulated before or after the heating step. By re-circulating the concentrated glucocorticosteroid suspension through a homogenizer 10, an unwanted increase in particle size may be avoided.

The homogenizer 10 is a device known in the art in which a suspension of a particulate material, here the glucocorticosteroid suspension, is subjected to an energetic shear as the suspension is forced to pass therethrough. The homogenizer provides a sufficiently high shear force to cause the break up of aggregates of particles in the suspension and a reduction in the solid particles sizes. A precise numerical range for the level of shear is not appropriate given that the level of shear will depend on the viscosity of the suspension. The homogenizer 10 may be an in-line high-shear homogenizer (e.g. a Silverson 150 L) or, for more efficient and better particle size reduction, a high-pressure homogenizer (e.g. a Niro Panda). A high-shear homogeniser typically has a mixing workhead comprising rotatable rotor blades and a perforated stator with the rotor blades located within the stator. A high-pressure homogeniser typically comprises a pump, which can supply pressures up to about 1500 bar, and one or more interaction chambers where the passage of fluid through minute flow passages under high pressure and controlled flow action subjects the fluid to conditions of high turbulence and shear.

Figure 4:
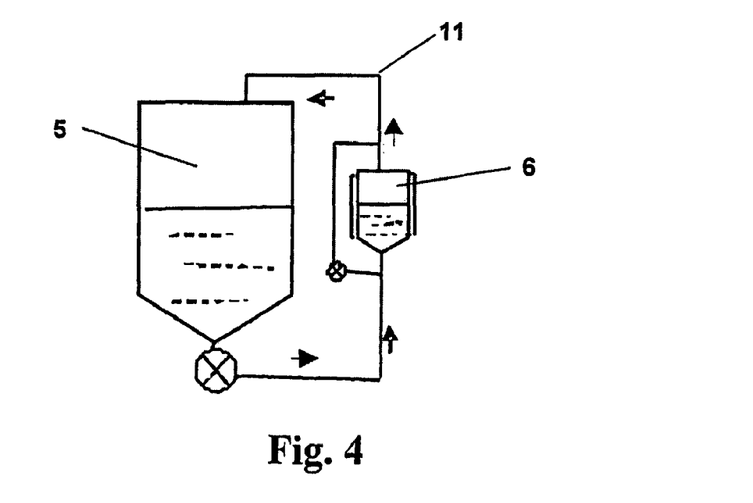
Figure 5:
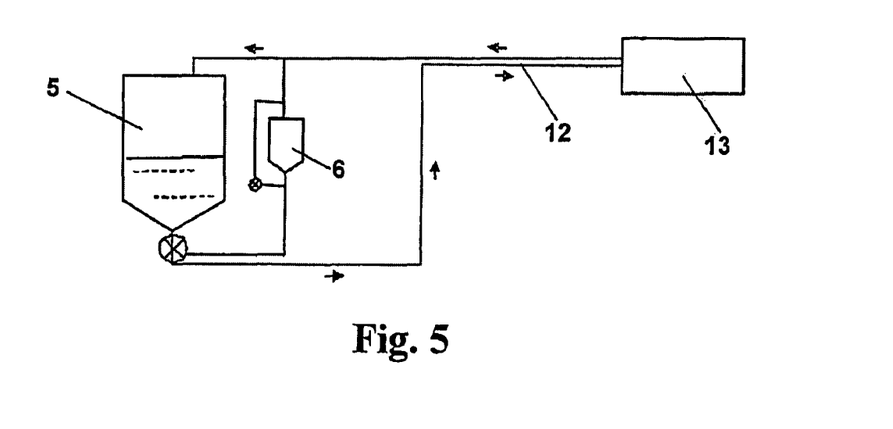

The sterilized glucocorticosteroid suspension is then mixed with the sterile water or sterile excipient solution held within the second vessel 5 via a re-circulation line 11 to form a diluted sterilized glucocorticosteroid suspension, as shown in FIG. 4. Typically the glucocorticosteroid suspension is diluted with the sterile water or sterile excipient liquid to a pharmaceutically suitable concentration. Preferably re-circulation is performed for about 45 mins. The diluted glucocorticosteroid suspension is held within second vessel 5 until required for filling. During the hold of the suspension it is continually circulated via re-circulation line 12 between second vessel 5 and BFS machine 13 to maintain the active material in suspension, as shown in FIG. 5. BFS machines are well known in the art and are exemplified by Rommelag Blow Fill Seal 3012, 305 and 4010 machines and Weiler Engineering ASEP-TECH Blow Fill Seal 624, 628 and 640 machines.

Prior to filling, BFS machine 13 is sterilized, e.g. by steam at temperatures of about 122° C. to about 138° C. for not less than 30 mins. The BFS machine 13 may use any pharmaceutically acceptable primary container material. Typically low-density polyethylene granulate is used to form the primary container/closure system on the BFS machine 13 although high-density polyethylene, polypropylene, poly vinyl chloride or polyethylene terephthalate may also be used. Mixtures of these materials may also be used. The BFS machine 13 is configured to present open topped units to the filling head for each machine filling cycle. The sterile glucocorticosteroid suspension is filled into the formed units through a time/pressure/dosing unit which delivers a precise measure of the suspension via filling needles. Following filling the filling needles are withdrawn and the head section of the mould closes to seal the units completely. The filled units are then removed from the BFS machine 13.

To be "sterile" means that a product or composition meets the criteria of sterility according to the US Pharmacopoeia 27/NF22, 2004, or its counterpart in other jurisdictions, and which provides a therapeutically acceptable glucocorticosteroid and/or pharmaceutical formulation.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable, which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

The methods and compositions of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

Another aspect of the invention provides suspension compositions of sterilized glucocorticosteroids prepared according to the methods of the first aspect of the invention described above. In some embodiments, the composition is a pharmaceutical composition for treating or alleviating the symptoms of allergic and/or inflammatory conditions in a mammalian patient. In these embodiments, the compositions comprise a therapeutically effective amount of sterilized, labile glucocorticosteroid(s) in a pharmaceutically acceptable vehicle.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. The invention therefore provides a method to tailor the administration/treatment to the particular exigencies specific to a given mammal.

Other embodiments contemplate compositions presenting the glucocorticosteroid in combination with a second active ingredient. In some embodiments, the second active ingredient may be selected from albuterol, ipratropium bromide, cromolyn, formoterol, tiotropium, oxitropium and azelastine.

In yet other embodiments of this aspect, the compositions of the invention are formulated to be suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal) administration. Preferably the composition is formulated for inhalation in which case the particle size of the glucocorticosteroid is preferably such that the Dv100 is less than 20 μm, the Dv90 is less than 10 μm and the Dv50 is less than 5 μm, where Dvn represents the volume diameter at the nth percentile. The volume diameter is a known term in the art and indicates die diameter that a sphere would have when it has the volume of the particle. The particle sizes may be measured by standard techniques, such as by laser diffraction as described in the examples hereinbelow. Such a particle sizes may be achieved using the heat sterlisation conditions as described herein.

The formulations of the compositions of the invention may conveniently be presented in unit dosage form and may be prepared by conventional pharmaceutical techniques. Such techniques include the step of bringing into association the compounds of the invention and the pharmaceutically acceptable carrier(s), such as a diluent or an excipient. In general, the compositions are prepared by uniformly and intimately bringing into association the active ingredient with liquid or finely divided solid carriers or both, and then, if necessary, shaping the product.

The sterile glucocorticosteroids prepared according to the invention are optionally formulated in a pharmaceutically acceptable vehicle with any of the well known pharmaceutically acceptable carriers, including diluents and excipients (see *Remington's Pharmaceutical Sciences*, $18^{th}$ Ed., Gennaro, Mack Publishing Co., Easton, Pa. 1990 and *Remington: The Science and Practice of Pharmacy*, Lippincott, Williams & Wilkins, 1995). The type of pharmaceutically acceptable carrier/vehicle employed in generating the compositions of this aspect of the invention will vary depending upon the mode of administration of the composition to the mammal. Generally, pharmaceutically acceptable carriers are physiologically inert and non-toxic. Formulations of compositions according to the invention may contain more than one type of pharmacologically active ingredient useful for the treatment of the symptom/condition being treated.

In yet another aspect, the invention provides methods for using compositions of the invention for treating or alleviating the symptoms of allergic and/or inflammatory conditions in a mammalian patient. Such methods comprise the administration of a therapeutically effective amount of the labile glucocorticosteroid in a pharmaceutically acceptable vehicle. In various embodiments of this aspect, administration of a therapeutically effective amount of the glucocorticosteroid, either alone or in combination with a second active agent, is by oral, inhalation, rectal, ophthalmic, vaginal, or parenteral administration. In some embodiments, the glucocorticosteroid is budesonide while in yet other embodiments the glucocorticosteroid is beclomethasone.

The invention further provides a sterile glucocorticosteroid, preferably an anti-inflammatory glucocorticosteroid, for use in the treatment of allergic and/or inflammatory conditions. The allergic and/or inflammatory conditions to be treated need not be confined to one anatomic site, for example, the nose or lungs, and the compositions of the invention are formulated for administration appropriate to the site of treatment. Allergic and/or inflammatory conditions include, without limitation, contact dermatitis, asthma, rhinitis, or chronic obstructive pulmonary disease. The invention also provides for the use of sterile glucocorticosteroid compositions, in the manufacture of a medicament (preferably a sterile medicament) for use in the treatment of allergic and/or inflammatory conditions.

The following examples are intended to illustrate further certain embodiments of the invention and are not limiting in nature. Those skilled in the art will recognize, or be able to ascertain, using no more than routine experimentation, numerous equivalents to the specific substances and procedures described herein.

EXAMPLES

Examples 1 to 3

Heat Sterilization of Budesonide

Three batches of a sterile budesonide suspension were prepared. Example 1 (applicant's batch W15711) contained 0.125 mg/ml of budesonide, Example 2 (applicant's batch W15641) contained 0.25 mg/ml of budesonide and Example 3 (applicant's batch Z00581) contained 0.5 mg/ml of budesonide.

A 500 L stainless steel mixing vessel was cleaned using hot water for injections (WFI) and steam sanitized. WFI at 25° C. was added to the vessel. The vessel was then charged with the following excipients in the following order: sodium chloride USP, citric acid monohydrate USP, tri-sodium citrate dihydrate USP, disodium edetate dihydrate USP and Polysorbate 80 USP from an additions hopper. For Examples 1 and 3, 80 g of Polysorbate 80 was added at this stage. For Example 2, 30 g of Polysorbate 80 was added at this stage. The quantities of each component are set out in Table 1. The solution was then re-circulated through a mixer and a stainless-steel line for 10 mins to ensure complete dissolution. During circulation, the additions hopper was rinsed with the circulating solution.

TABLE 1

Materials in whole batch

|  | Example 1 | Example 2 | Example 3 |
| --- | --- | --- | --- |
| Water for Injection | 500 kg | 250 kg | 500 kg |
| Sodium Chloride | 4250 g | 2125 g | 4250 g |
| Citric Acid Monohydrate | 155 g | 77.5 g | 155 g |
| Tri-Sodium Citrate Dihydrate | 250 g | 125 g | 250 g |
| Disodium Edetate Dihydrate | 50 g | 25 g | 50 g |
| Polysorbate 80 | 100 g | 50 g | 100 g |

A stainless steel 500 L excipient vessel and stainless steel 4 L concentrate vessel were cleaned and sterilized in place, using hot WFI followed by steam.

The excipient and concentrate vessels were charged with the excipient liquid having been passed via a sterilizing grade filter (0.1 μm Fluorodyne PVDF filter, PALL Europe Limited). The concentrate vessel was isolated and additional 20 g of Polysorbate 80 was added. The composition of the concentrated suspension is set out in Table 2.

TABLE 2

Materials in drug concentrate (portion of batch which was heat sterilized)

|  | Example 1 | Example 2 | Example 3 |
| --- | --- | --- | --- |
| Water for Injection | 4 kg | 4 kg | 4 kg |
| Budesonide | 66.7 g | 64.1 g | 251.2 g |
| Sodium Chloride | 34 g | 34 g | 34 g |
| Citric Acid Monohydrate | 1.24 g | 1.24 g | 1.24 g |
| Tri-Sodium Citrate Dihydrate | 2 g | 2 g | 2 g |
| Disodium Edetate Dihydrate | 0.4 g | 0.4 g | 0.4 g |
| Polysorbate 80 | 20.64 g | 20.48 g | 20.64 g |

The concentrated suspension was then sterilized under the conditions set out in Table 3. Before, during and after the sterilization, the concentrated suspension was re-circulated through a Silverson 150 L homogenizer via a stainless steel re-circulation line.

TABLE 3

Sterilisation conditions

|  | Example 1 | Example 2 | Example 3 |
| --- | --- | --- | --- |
| Temperature | 126-129° C. | 124-129° C. | 124-132° C. |
| Time | 32 min | 32 min | 32 min |

The sterilized glucocorticosteroid suspension was then mixed with the sterile excipient solution held in the excipient vessel to form a diluted sterilized budesonide suspension. The final product strength was 0.125 mg/ml for the suspension of Example 1, 0.25 mg/ml for the suspension of Example 2 and 0.5 mg/ml for the suspension of Example 3.

A sample of the suspension was analysed for related substances/impurities using HPLC and the results are set out in Table 4. The analysis of the suspension showed pharmaceutically acceptable level of impurities.

TABLE 4

Related substances/impurities after sterilization (wt % based on the amount of budesonide)

|  | Example 1 | Example 2 | Example 3 |
| --- | --- | --- | --- |
| 21-dehydro-budesonide | 0.11 | 0.11 | 0.08 |
| Desonide | ND | ND | ND |
| 16α-hydroxypredinisolone | <0.05 | ND | ND |
| Budesonide 1,2 dihydro | ND | ND | ND |
| 22-Methyl homologue | ND | ND | <0.05 |
| D-homobudesonide | ND | ND | <0.05 |
| 14,15-dehydrobudesonide | ND | ND | ND |
| S-11-Keto budesonide | <0.05 | <0.05 | <0.05 |
| R-11-Keto budesonide | <0.05 | <0.05 | <0.05 |
| S-21-Acetate budesonide | ND | ND | ND |
| R-21-Acetate budesonide | ND | ND | ND |
| Maximum individual unknown | <0.05 | <0.05 | <0.05 |
| Total Impurities | 0.11 | 0.11 | 0.08 |

(ND = Not Detected, <0.05 = Reporting Level)

The diluted suspension was continually circulated via a Rommelag 3012 BFS machine and packaged into containers using low-density polyethylene.

Samples of the suspension were analysed for particle size distribution by laser light diffraction using a Malvern Mastersizer S. The parameters considered are the volumetric diameters in μm of the $10^{th}$, $50^{th}$ and $90^{th}$ percentiles of the particles, expressed as Dv10, Dv50 and Dv90 respectively, which are determined by assuming that the particles have a geometric shape equivalent to a sphere. The results are set out in Table 5.

TABLE 5

Particle size distribution after sterilization

|  | Example 1 | Example 2 | Example 3 |
| --- | --- | --- | --- |
| Dv10 | 0.6 | 0.6 | 0.7 |
| Dv50 | 2.3 | 2.5 | 2.7 |
| Dv90 | 4.7 | 5.4 | 5.6 |

The particle size distributions obtained are within the recognised region required for effective delivery in Inhalation products.

The batches were submitted to the sterility test and complied with the sterility requirements of Ph. Eur. and USP.

Examples 4 and 5

Heat Sterilization of BDP

Two batches of a sterile BDP (Beclomethasone Dipropionate) suspension were prepared. Example 4 (applicant's batch W16531) and Example 5 (applicant's batch W17211) both contained 0.4 mg/1 ml of BDP.

A 500 L stainless steel mixing vessel was cleaned using hot water for injections (WFI) and steam sanitized. WFI at 25° C. was added to the vessel. The vessel was then charged with the following excipients in the following order: sodium chloride EP, Polysorbate 20 EP, and Span 20 EP from an additions hopper. For Example 4, 400 g of Polysorbate 20 was added at this stage. For Example 5, 475 g of Polysorbate 20 and 95 g of Span 20 were added at this stage. The quantities of each component are set out in Table 6. The solution was then re-circulated through a mixer and a stainless-steel line for 10 mins to ensure complete dissolution. During circulation, the additions hopper was rinsed with the circulating solution.

TABLE 6

Materials in whole batch

|  | Example 4 | Example 5 |
|---|---|---|
| Water for Injection | 500 kg | 500 kg |
| Sodium Chloride | 4500 g | 4500 g |
| Polysorbate 20 | 500 g | 500 g |
| Span 20 | 100 g | 100 g |

A stainless steel 500 L excipient vessel and stainless steel 4 L concentrate vessel were cleaned and sterilized in place, using hot WFI followed by steam.

The excipient and concentrate vessels were charged with the excipient liquid having been passed via a sterilizing grade filter (Example 4—0.1 μm Fluorodyne PVDF filter, PALL Europe Limited Example 5—0.2 μm Fluorodyne PVDF filter, PALL Europe Limited). The concentrate vessel was isolated and an additional Polysorbate 20 (100 g for Example 4, 25 g for Example 5) and Span 20 (100 g for Example 4, 5 g for Example 5) was added. The composition of the concentrated suspension is set out in Table 7.

TABLE 7

Materials in drug concentrate (portion of batch which was heat sterilized)

|  | Example 4 | Example 5 |
|---|---|---|
| Water for Injection | 4 kg | 4 kg |
| BDP | 206 g | 210 g |
| Sodium Chloride | 36 g | 36 g |
| Polysorbate 20 | 103.2 g | 28.8 g |
| Span 20 | 100 g | 5.8 g |

The concentrated suspension was then sterilized under the conditions set out in Table 8. Before and during the sterilization, the concentrated suspension was re-circulated through a lobe pump via a stainless steel re-circulation line. After sterilisation the concentrated suspension was re-circulated through a homogeniser via the lobe pump and stainless steel re-circulation line.

TABLE 8

Sterilisation conditions

|  | Example 4 | Example 5 |
|---|---|---|
| Temperature | 124-132° C. | 124-132° C. |
| Time | 32 min | 32 min |

The sterilized glucocorticosteroid suspension was then mixed with the sterile excipient solution held in the excipient vessel to form a diluted sterilized BDP suspension. The final product strength was 0.4 mg/ml for the suspension of Example 4 and Example 5.

A sample of the suspension was analysed for related substances/impurities using HPLC and the results are set out in Table 9. The analysis of the suspension showed pharmaceutically acceptable level of impurities.

TABLE 9

Related substances/impurities after sterilization (wt % based on the amount of BDP)

|  | Example 4 | Example 5 |
|---|---|---|
| Beclomethasone | ND | ND |
| Beclomethasone 17 Propionate | 0.05 | ND |
| Beclomethasone 21 Propionate | ND | ND |
| Beclomethasone 21 Acetate 21 Propionate | ND | ND |
| Beclomethasone Dipropionate 9β, 11 epoxy analogβ | 0.60 | 0.12 |
| Beclomethasone Dipropionate 9 bromo analog | ND | ND |
| Beclomethasone Dipropionate δ9, 11 analog | ND | ND |
| Beclomethasone Dipropionate 21 Butyrate | ND | ND |
| Beclomethasone Dipropionate 6α chloro | ND | ND |
| Beclomethasone Dipropionate 6α bromo | ND | ND |
| Maximum individual unknown | 0.12 | 0.08 |
| Total Impurities | 0.89 | 0.20 |

(ND = Not Detected)

The diluted suspension was continually circulated via a BFS machine and packaged into containers using low-density polyethylene.

Samples of the suspension were analysed for particle size distribution by laser light diffraction using a Malvern Mastersizer S. The parameters considered are the volumetric diameters in μm of the $10^{th}$, $50^{th}$ and $90^{th}$ percentiles of the particles, expressed as Dv10, Dv50 and Dv90 respectively, which are determined by assuming that the particles have a geometric shape equivalent to a sphere. The results are set out in Table 10.

TABLE 10

Particle size distribution after sterilization

|  | Example 4 | Example 5 |
|---|---|---|
| Dv10 | 0.4 | 0.4 |
| Dv50 | 1.4 | 1.5 |
| Dv90 | 3.6 | 3.6 |

The particle size distributions obtained are within the recognised region required for effective delivery in Inhalation products.

The batches were submitted to the sterility test and complied with the sterility requirements of Ph. Eur.

What is claimed is:

1. A method for preparing a sterile suspension of a glucocorticosteroid comprising the following steps:
   (i) heating a glucocorticosteroid suspension comprising a glucocorticosteroid, water and a surfactant in a mixing vessel to sterilize the glucocorticosteroid suspension,
   (ii) re-circulating the glucocorticosteroid suspension via a homogenizer before, during and/or after step (i), and subsequently
   (iii) mixing the glucocorticosteroid suspension with sterile water or a sterile excipient liquid comprising water and one or more pharmaceutically acceptable excipients;
   wherein the heating is carried out for at least 2 minutes.

2. A method as claimed in claim 1, wherein the sterile water or sterile excipient liquid is prepared by passing water or an excipient liquid through a sterilizing grade filter.

3. A method as claimed in claim 1, wherein the sterile excipient liquid is used and the one or more pharmaceutically acceptable excipients comprises a surfactant.

4. A method as claimed in claim 1, wherein the sterile excipient liquid is used and the one or more pharmaceutically acceptable excipients comprises at least one of a buffer, a salt, a wetting agent, a stabilizing agent and an isotonic agent.

5. A method as claimed in claim 1, wherein the re-circulating in step (ii) occurs during the heating in step (i).

6. A method as claimed in claim 1, wherein the concentration of the glucocorticosteroid in the glucocorticosteroid suspension is from about 15 to about 300 mg/ml.

7. A method as claimed in claim 1, wherein at least 50% of the glucocorticosteroid in the glucocorticosteroid suspension is in the form of a suspension during heating.

8. A method as claim in 7, wherein at least 60% of the glucocorticosteroid in the glucocorticosteroid suspension is in the form of a suspension during heating.

9. A method as claimed in claim 1, wherein the glucocorticosteroid is selected from the group consisting of at least one of beclomethasone, budesonide, ciclesonide, cortivazol, deflazacort, flumethasone, flunisolide, fluocinolone, fluticasone, mometasone, refleponide, tipredane and triamcinolone.

10. A method as claimed in claim 8, wherein the glucocorticosteroid is beclomethasone or budesonide.

11. A method as claimed in claim 3, wherein the concentration of the surfactant in the glucocorticosteroid suspension is from about 0.2 to about 300 mg/ml.

12. A method as claimed in claim 1, wherein heating is carried out at a temperature of from about 101° C. to about 145° C.

13. A method as claimed in claim 12, wherein heating is carried out at a temperature of from about 122° C. to about 138° C.

14. A method as claimed in claim 1, wherein heating is carried out for about 2 to about 180 mins.

15. A method as claimed in claim 14, wherein heating is carried out for at least about 30 mins.

16. A method as claimed in claim 1, wherein the homogenizer is an in-line homogenizer or a high-pressure homogenizer.

17. A method as claimed in claim 1, wherein, in step (iii), the sterile excipient liquid is used and the glucocorticosteroid suspension is diluted with the sterile excipient liquid to a pharmaceutically suitable concentration.

18. A method as claimed in claim 1 further comprising, subsequent to step (iii), packaging the sterile suspension of a glucocorticosteroid.

19. A method as claimed in claim 18, wherein the sterile suspension of a glucocorticosteroid is packaged by a blow-fill-seal (BFS) machine.

* * * * *